United States Patent [19]
Dry

[11] Patent Number: 5,575,841
[45] Date of Patent: Nov. 19, 1996

[54] CEMENTITIOUS MATERIALS

[75] Inventor: Carolyn M. Dry, 1605 Park Haven Dr., Champaign, Ill. 61821

[73] Assignee: Carolyn M. Dry, Champaign, Ill.

[21] Appl. No.: 174,751

[22] Filed: Dec. 29, 1993

Related U.S. Application Data

[63] Continuation of Ser. No. 540,191, Jun. 19, 1990, abandoned.

[51] Int. Cl.$^6$ .............................. C04B 14/38; C04B 14/42
[52] U.S. Cl. ....................... 106/711; 106/677; 106/724; 106/802; 106/819; 106/823; 106/805; 428/320.2; 428/321.1; 428/321.5; 428/364
[58] Field of Search .............................. 106/677, 711, 106/727, 802, 819, 823; 428/320.2, 321.5, 321.1, 364, 375

[56] References Cited

U.S. PATENT DOCUMENTS

| | | | |
|---|---|---|---|
| 3,475,188 | 10/1969 | Woodhouse et al. | 106/58 |
| 3,505,244 | 4/1970 | Cessna | 252/391 |
| 3,704,264 | 11/1972 | German | 252/316 |
| 4,109,033 | 8/1978 | Blankenhorn | 427/314 |
| 4,587,279 | 5/1986 | Salyer et al. | 106/724 |
| 4,961,790 | 10/1990 | Smith et al. | 106/823 |

FOREIGN PATENT DOCUMENTS 0107086  5/1984  European Pat. Off. .

OTHER PUBLICATIONS

Time Magazine, Apr. 8, 1966, "Capsule Solution for Countless Problems", p. 70.
Kosmatka et al. "Design & Control of Concrete Mixtures", Thirteenth Edition, 1988 PCA, pp. 64–65 (no month).
Dry, C. M., "Building Materials Which Evolve and Adapt Over Time", Jun. 19, 1989.
Vigo, T. L. and Frost, C. M., "Temperature–Adaptable Hollow Fibers Containing Polyethylene Glycols" Apr., 1973 (no month).
Geishauser, C. B. and Cady, P. D., "A Study of the Heat Treating Cycle for Internally Sealed Concrete Containing Montan–Paraffin Wax Beads", 1977.

*Primary Examiner*—Mark L. Bell
*Assistant Examiner*—Michael Marcheschi
*Attorney, Agent, or Firm*—Hill, Steadman & Simpson

[57] ABSTRACT

A cementitious material, such as concrete, contains carriers having within them an agent for improving the physical properties of the cementitious material. The agent is released from the carriers into the cementitious material at a desired time after setting by the action of an external stimulus.

19 Claims, No Drawings

1

CEMENTITIOUS MATERIALS

This a continuation of application Ser. No. 07/540,191, filed Jun. 19, 1990, abandoned.

FIELD OF THE INVENTION

This invention relates to cementitious materials and other setting construction materials.

BACKGROUND OF THE INVENTION

Cement is a fine, gray powder consisting of alumina, lime, silica, and iron oxide which sets to a hard material after mixture with water. Cement, along with sand and stone aggregate, make up concrete, the most widely used building material in the world. Steel reinforcing bars (rebars) are commonly added to the interior of concrete for additional strength.

There are many reasons for the popularity of concrete. It is relatively inexpensive, capable of taking on the shape of a mold, exceptionally high in compression strength, and very durable when not exposed to repeated freeze-thaw cycles. However, whether or not reinforced, concrete is not without its drawbacks. One major drawback of concrete is that it is relatively low in tensile strength. In other words, it has little ability to bend, has little impact resistance, and is brittle. A second major drawback is that its durability is significantly reduced when exposed to repeated freeze-thaw cycles in the presence of water. Concrete is relatively porous and water is able to permeate the material. Freezing and thawing, with the accompanying expansion and contraction of the water, forms cracks in the concrete. Furthermore, if salt is also present in the environment, it dissolves in the water and permeates into the concrete where it induces corrosion of any rebars present.

Various techniques have been suggested for addressing these drawbacks. The addition of fibers to concrete has improved its tensile strength, but has decreased its compression strength. Coating the exterior surface of the concrete reduces water permeation, but is a time-consuming additional step and has little, if any, effect on the strength of the concrete. Accordingly, a demand still exists for a concrete with greater tensile strength, greater durability, and comparable compression strength.

SUMMARY OF THE INVENTION

A general object of this invention is to provide an improved cementitious material. A more particular object is to provide such a material having greater durability and greater tensile strength. Another general object of this invention is to provide a method of improving the durability and tensile strength of a cementitious material.

I have discovered an improved cementitious material. The material comprises carriers having within them an agent for improving the physical properties of the cementitious material. The agent is released from the carriers into the cementitious material at a desired time after setting by the action of an external stimulus. Representative agents are polymer impregnators, sealants, adhesives, water-barrier agents, anti-corrosion agents, antifreeze agents, and fiber-protecting agents.

I have also discovered a method of improving the physical properties of a cementitious material. The method comprises: (1) obtaining carriers having within them an agent for improving the physical properties of the cementitious material; (2) adding the agent-containing carriers to the cementitious material before it sets; and (3) releasing the agent from the carriers at a desired time after setting by the action of an external stimulus.

This invention enables cementitious materials, such as concrete, to be improved by the release of beneficial agents from within the material, where they do the most good, and at a time after setting when their release does the most good.

DETAILED DESCRIPTION OF THE INVENTION

A. Cementitious Materials

Cementitious materials are those having physical properties similar to cement, namely, they can be poured into a mold where they set up to a hard, porous matrix upon drying. While petroleum-based setting construction materials such as asphalt are suitable, the preferred cementitious materials are those containing cement, such as concrete.

B. Carriers

The carriers present in the cementitious material of this invention serve the primary purpose of housing the agents until they are released. The carriers are particles having pores or hollow internal spaces for holding the agents. Suitable carriers include porous aggregates such as vermiculite, finely crushed limestone, expanded clay, and the like. Other suitable carriers are paraffin wax and other moldable materials which melt at a relatively low temperature. Wax can be mixed with a variety of agents to form discrete particles, commonly known as prills. Additional suitable carriers are porous and/or hollow fibers of such materials as polypropylene, polyamides, glass, ceramic, cellulose, and the like. The fibers are individual, assembled in bundles, or woven. Carriers consisting of fibers of elastomeric materials are preferred when an increase in tensile strength is one of the primary goals. Representative of such materials is porous polypropylene tubing.

C. Agents

The agents suitable for use in this invention include a wide variety of materials which impart beneficial effects to the cementitious material after it has set to a hard, porous matrix.

One class of agents are polymerizable monomers such as methyl methacrylate and styrene which enhance the tensile strength and the compression strength of the cementitious material. These monomers have low viscosities which enable them to impregnate the pores of the cementitious material. They also have low toxicities and relatively high boiling points, readily polymerize at elevated temperatures, and are inexpensive. The polymerized compounds fill the pores and provide an added measure of flexibility and strength to the matrix.

A second class of agents are sealants which fill up the pores, drive water to the surface, and decrease the permeability of the cementitious material. Reducing permeability increases durability by minimizing the damaging effects of freeze-thaw cycles. While tensile-strength enhancers also function as sealants, there are many effective sealants which have little, if any, effect on tensile strength.

A third class of agents are adhesives which improve the bonding of the carriers to the cementitious material matrix.

A fourth class of suitable agents are crystalline compounds which block the flow of water through pores. Such water-barrier compounds include Salt Guard, a siloxane sold by Pro So Co., Inc. of Kansas City, Kans.; and Xypex, a sodium silicate sold by Xypex Corporation. Xypex is a preferred agent because it forms crystals in the cementitious material which permit water vapor to escape, but which prevent liquid water from entering.

A fifth class of agents are anti-corrosion agents. The corrosion of rebars in cementitious materials is an expansive reaction which causes cracking. A well known and effective anti-corrosion agent is calcium nitrite. Corrosion of the carriers can also be reduced with the use of an appropriate agent.

A sixth class of agents are antifreeze compounds such as propylene glycol which, when mixed with water, form a solution having a lower freezing point. Propylene glycol is widely used in automobile radiators for this purpose. By depressing the freezing point, the deleterious effects of freeze-thaw cycles are reduced or eliminated.

A seventh class of agents are those which protect fibers against degradation. For example, compounds are commercially available which protect fiberglass against degradation in highly alkaline environments.

The agents may be in the form of solid, liquid, or gas and are used individually or in combination when more than one beneficial effect upon the cementitious material is desired. The concentration of carrier and agent to use in a given application is a matter of choice which depends upon economics and the properties sought to be enhanced. Generally, the carrier and agent are initially present at less than about 10 volume percent of the matrix, preferably less than about 5 volume percent. As the concentration of carrier and agent increases, there is generally a loss of compression strength.

D. Release of Agents

The agents forming a part of the cementitious material of this invention are released from the carriers into the material in direct response to the intrusion of the environment. This enables the agents to appear at the time and place to give the greatest benefit. A variety of mechanisms are available to accomplish this result.

One of the simpler methods is to coat the agent-containing carrier with paraffin wax or other low-melting compound. The agent is then released by heating the cementitious material and carriers at the desired time. For example, in the case of tensile-strength enhancers such as styrene or methyl methacrylate, their polymerization into the pores optimally occurs about 10 to 50 days after the cementitious material sets.

A second mechanism for release of the agents is advantageously used with anti-corrosion agents. It is known that the corrosion of rebars in reinforced concrete commences when the pH of the concrete drops to about 11.5. Coatings are commercially available which are pH sensitive. Accordingly, coating an anti-corrosion agent with a material which degrades at about pH 11.5 ensures that the anti-corrosion agent is released at exactly the best time to counteract the corrosion of the rebars.

A third method of release is to coat a sealing agent with a thin brittle material which will itself crack as the cementitious material cracks. Brittle coatings such as shellac perform well in such applications.

Fourthly, when employing an agent which is best released slowly over a period of time, a coating can be chosen which dissolves slowly in the alkaline environment of the setting cementitious material. A variety of polyols serve this purpose well.

Finally, liquids absorbed in porous aggregate materials are squeezed out during freeze thaw cycles. Accordingly, antifreeze agents such as propylene glycol can be released at an optimal time into the cementitious material.

E. Examples

The following examples are illustrative only and describe work, some of which was performed with the support of the U.S. Government under University of Illinois contract number RCT 366A-C409-89 awarded by the Department of the Army. The U.S. Government may have certain rights in this invention.

EXAMPLE 1

This Example illustrates the preparation of sealed polypropylene fibers.

Porous polypropylene fiber tubing having an inside diameter of 400 microns, a porosity of 40%, and sold under the trademark X-20 was obtained from the Separations Product Division of Hoechst Celanese Corporation, Charlotte, N.C. One portion of the tubing was set aside and a second portion was filled with agent as follows. Equal weight amounts of the tubing and an agent (calcium nitrite or methyl methacrylate) were added to a vacuum flask. The flask was sealed and then evacuated to draw the chemical agent into the fibers. After about one hour, the vacuum was released and the agent-containing tubing was removed. The hollow tubing (set aside earlier) and the agent-containing tubing were then dipped briefly into a molten paraffin wax bath to apply a thin, wax coating to the tubing. The tubing was then cut into sections having a length of about 25 mm using a heated, wax-covered blade which sealed the sections as they were cut.

EXAMPLE 2

This Example illustrates the preparation of cement samples.

White cement was mixed with water at a set weight ratio. Varying concentrations of hollow and filled fiber sections from Example 1 were then added and dispersed. The mixtures were then poured into three different molds: a cube having the dimensions of 2×2×2 inches, a prism having the dimensions of 1×1×6 inches, and a cylinder having a diameter of 1.5 inches and a length of 0.75 inches.

The samples were cured as follows. While still in the molds, they were placed into a curing chamber at 85° F. and a relative humidity of 100%. After 24 hours, the samples were removed from the molds and then returned to the curing chamber for an additional 2 days.

After curing, the samples were tested or heated before testing in one of three different ways: (1) At 120° F. for one-half hour; (2) At 212° F. for one-half hour; and (3) At high power in a microwave oven for two minutes.

EXAMPLE 3

This Example illustrates the effect of polypropylene fibers on the compression strength, bending, and permeability of cement.

Compression strength was tested using the cube samples of Example 2 in the standard ASTM Test Method. Bending was tested using the prism samples in the ASTM Test Method. Permeability was tested using the cylinder samples in the ASTM Test Method. The results are presented in the following table.

| Number of Fibers | Fiber Filling[1] | Heat Treatment[2] | Compression (psi) | Bending (psi) | Permeability (ml/hr) |
| --- | --- | --- | --- | --- | --- |
| 75 | C.N. | M.W. | — | 43 | — |
| 150 | C.N. | M.W. | — | 35 | — |
| 225 | C.N. | M.W. | — | 39 | — |
| 300 | C.N. | M.W. | — | 39 | — |
| 75 | None | M.W. | — | 59 | — |
| 225 | None | M.W. | — | 39 | — |
| 300 | None | M.W. | — | 39 | — |
| 75 | C.N. | M.W. | 5799 | — | — |
| 150 | C.N. | M.W. | 5092 | — | — |
| 225 | C.N. | M.W. | 5231 | — | — |
| 300 | C.N. | M.W. | 4351 | — | — |
| 75 | None | M.W. | 4385 | — | — |
| 150 | None | M.W. | 5384 | — | — |
| 225 | None | M.W. | 4988 | — | — |
| 300 | None | M.W. | 4904 | — | — |
| 0 | None | 120° | 5382 | — | — |
| 75 | None | 120° | 5609 | — | — |
| 75 | C.N. | 120° | 6055 | — | — |
| 150 | C.N. | 120° | 5360 | — | — |
| 225 | C.N. | 120° | 5527 | — | — |
| 300 | C.N. | 120° | 4856 | — | — |
| 75 | C.N. | 120° | — | 49 | — |
| 150 | C.N. | 120° | — | 43 | — |
| 225 | C.N. | 120° | — | 43 | — |
| 300 | C.N. | 120° | — | 35 | — |
| 0 | None | 120° | — | 33 | — |
| 75 | None | 120° | — | 31 | — |
| 0 | C.N. | None | — | 43 | — |
| 70 | C.N. | None | — | 43 | — |
| 150 | C.N. | None | — | 43 | — |
| 175 | C.N. | None | — | 43 | — |
| 225 | C.N. | None | — | 35 | — |
| 0 | C.N. | None | 5255 | — | — |
| 100 | C.N. | None | 5305 | — | — |
| 150 | C.N. | None | 4123 | — | — |
| 200 | C.N. | None | 5196 | — | — |
| 225 | C.N. | None | 4375 | — | — |
| 25 | C.N. | 120° | — | — | 1.5 |
| 50 | C.N. | 120° | — | — | 1.9 |
| 75 | C.N. | 120° | — | — | 2.0 |
| 100 | C.N. | 120° | — | — | 2.0 |
| 0 | None | 120° | — | — | 0.5 |
| 0 | None | None | — | — | 0.5 |
| 25 | None | 120° | — | — | 1.0 |
| 75 | C.N. | M.W. | — | 43 | — |
| 100 | C.N. | M.W. | — | 35 | — |
| 225 | C.N. | M.W. | — | 39 | — |
| 300 | C.N. | M.W. | — | 39 | — |
| 75 | None | M.W. | — | 48 | — |
| 100 | None | M.W. | — | 39 | — |
| 225 | None | M.W. | — | 39 | — |
| 300 | None | M.W. | — | 39 | — |
| 75 | C.N. | M.W. | 5799 | — | — |
| 150 | C.N. | M.W. | 5092 | — | — |
| 225 | C.N. | M.W. | 5231 | — | — |
| 300 | C.N. | M.W. | 4351 | — | — |
| 75 | None | M.W. | 4385 | — | — |
| 75 | None | M.W. | 5384 | — | — |
| 150 | None | M.W. | 4988 | — | — |
| 225 | None | M.W. | 4904 | — | — |
| 50 | M.M. | 212° | 5463 | — | — |
| 100 | M.M. | 212° | 5325 | — | — |
| 150 | M.M. | 212° | 5626 | — | — |
| 200 | M.M. | 212° | 5310 | — | — |
| 250 | M.M. | 212° | 4454 | — | — |
| 35 | M.M. | 212° | — | 39 | — |
| 70 | M.M. | 212° | — | 30 | — |
| 105 | M.M. | 212° | — | 39 | — |
| 140 | M.M. | 212° | — | 48 | — |
| 175 | M.M. | 212° | — | 43 | — |
| 50 | None | 212° | 517 | — | — |
| 100 | None | 212° | 4721 | — | — |
| 150 | None | 212° | 5250 | — | — |
| 200 | None | 212° | 4959 | — | — |
| 250 | None | 212° | 5300 | — | — |
| 0 | None | 212° | — | 26 | — |
| 35 | None | 212° | — | 43 | — |
| 105 | None | 212° | — | 39 | — |
| 175 | None | 212° | — | 26 | — |
| 0 | None | None | 5255 | — | — |
| 100 | None | None | 5305 | — | — |
| 150 | None | None | 4123 | — | — |
| 200 | None | None | 5196 | — | — |
| 225 | None | None | 4375 | — | — |
| 0 | None | None | — | 43 | — |
| 70 | None | None | — | 43 | — |
| 150 | None | None | — | 43 | — |
| 175 | None | None | — | 43 | — |
| 226 | None | None | — | 35 | — |
| 0 | M.M. | 120° | 5206 | — | — |
| 75 | M.M. | 120° | 4904 | — | — |
| 150 | M.M. | 120° | 4493 | — | — |
| 225 | M.M. | 120° | 5003 | — | — |
| 300 | M.M. | 120° | 3070 | — | — |
| 0 | M.M. | 120° | — | 30 | — |
| 75 | M.M. | 120° | — | 35 | — |
| 150 | M.M. | 120° | — | 35 | — |
| 225 | M.M. | 120° | — | 35 | — |
| 300 | M.M. | 120° | — | 30 | — |
| 0 | None | 120° | 5205 | — | — |
| 75 | None | 120° | 5087 | — | — |
| 150 | None | 120° | 5369 | — | — |
| 225 | None | 120° | 5275 | — | — |
| 0 | None | 120° | — | 30 | — |
| 75 | None | 120° | — | 43 | — |
| 150 | None | 120° | — | 30 | — |
| 225 | None | 120° | — | 30 | — |
| 0 | M.M. | 120° | — | — | 1.0 |
| 25 | M.M. | 120° | — | — | 1.5 |
| 50 | M.M. | 120° | — | — | 0.5 |
| 75 | M.M. | 120° | — | — | 0.5 |
| 100 | M.M. | 120° | — | — | — |
| 0 | None | 120° | — | — | — |
| 25 | None | 120° | — | — | 1.0 |

[1]C.N. - calcium nitrite; M.M. - methyl methacrylate.
[2]Temperatures in degrees Fahrenheit; M.W. - microwave.

I claim:

1. A shaped article comprising:
   a cured matrix material having a plurality of hollow fibers dispersed therein, said hollow fibers having a releasable modifying agent contained therein, means for maintaining the modifying agent within the fibers until released and means for permitting release of the modifying agent from the hollow fibers into the matrix material in response to at least one external stimulus.

2. A shaped article as defined in claim 1, wherein said matrix material is a settable construction material.

3. A shaped article as defined in claim 1, wherein said matrix material is a cementitious material.

4. A shaped article as defined in claim 1, wherein said hollow fibers comprises of polypropylene, polyamide, glass ceramic or cellulose hollow fibers.

5. A shaped article as defined in claim 1, wherein said hollow fibers are elastomeric.

6. A shaped article as defined in claim 1, wherein said hollow fibers are porous polypropyrlene.

7. A shaped article as defined in claim 1, wherein said modifying agent is a liquid.

8. A shaped article as defined in claim 1, wherein said modifying agent comprises impregnators, sealants, adhesives, water barriers, anti-corrosion agents, anti-freeze agents or fiber protection modifying agents.

9. A shaped article as defined in claim 1, wherein said means for maintaining the modifying agent within the fibers comprises a coating material disposed on said fibers.

10. A shaped article as defined in claim 1, wherein said modifying agent filled hollow fibers comprise less than about 10 volume percent of said matrix material.

11. A shaped article as define in claim 1, wherein said matrix material is an inorganic matrix material.

12. A method for making a shaped article comprising the steps of preparing a curable matrix material in an uncured state; adding to the uncured matrix material at least one hollow fiber, said hollow fiber having a releasable modifying agent contained therein, said fiber further having means for maintaining the modifying agent within the fiber until released and means for permitting release of the modifying agent from the hollow fiber into the matrix material after cure in response to at least one external stimulus; and shaping and curing the matrix material and fiber to provide a shaped article.

13. An additive for improving final, cured properties of a curable matrix composition, maid additive comprising:

a hollow faber having a releasable modifying agent contained therein, means for maintaining the modifying agent within the fibers until released and means for permitting release of modifying agent from the hollow fibers into a matrix material in which the hollow fiber has been added in response to at least one external stimulus.

14. An additive as defined in claim 13, wherein the hollow fiber comprises polypropylene, polyamide, glass, ceramic or cellulose fibers.

15. An additive as defined in claim 13, wherein said hollow fiber is a porous material.

16. An additive as defined in claim 13, wherein said modifying agent is a liquid.

17. An additive as defined in claim 16, wherein said means for maintaining the modifying agent within the fiber until released comprises a coating material on the filled fiber.

18. An additive as defined in claim 13, wherein said modifying agent comprises impregnators, sealants, adhesives, water barriers, anti-corrosion agents, anti-freeze agents or fiber protection modifying agents.

19. A shaped article as defined in claim 1, wherein said hollow fibers are glass.

\* \* \* \* \*